United States Patent
Spyropoulos et al.

(10) Patent No.: US 6,451,905 B2
(45) Date of Patent: *Sep. 17, 2002

(54) SHEAR STABLE AMINOSILICONE EMULSIONS

(75) Inventors: Kostantinos Spyropoulos, Mies (CH); Sue L. Yang, Thornwood; Angelo J. Sabia, Yorktown Heights, both of NY (US); Joseph Pavlenyi, Amherst (CA)

(73) Assignee: Crompton Corporation, Middlebury, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,330

(22) Filed: Feb. 16, 1999

(51) Int. Cl.[7] ........................ C08L 83/08; C08G 77/26
(52) U.S. Cl. ...................... 524/588; 524/284; 524/287; 524/296; 524/291; 524/292; 524/300; 524/417; 524/421; 524/422; 524/429; 524/837; 524/838; 8/115.6; 8/115.7; 8/116.1; 162/80; 252/8.61; 252/8.63; 528/33; 528/38
(58) Field of Search ................... 524/588, 837, 524/838, 284, 287, 290, 291, 292, 300, 421, 422, 429, 417; 8/115.6, 115.7, 116.1; 162/80; 252/8.63, 8.61; 528/33, 38

(56) References Cited

U.S. PATENT DOCUMENTS

| | | | |
|---|---|---|---|
| 4,601,902 A | | 7/1986 | Ftidd et al. |
| 4,620,878 A | | 11/1986 | Gee |
| 4,894,412 A | | 1/1990 | Okada et al. |
| 5,057,572 A | * | 10/1991 | Chrobaczek et al. ........ 524/588 |
| 5,571,442 A | * | 11/1996 | Masaki et al. ............. 252/8.62 |
| 5,573,694 A | * | 11/1996 | Danner ....................... 252/8.63 |
| 5,683,625 A | | 11/1997 | Berthiaume et al. |
| 5,712,343 A | | 1/1998 | Geek et al. |

FOREIGN PATENT DOCUMENTS

EP       0 404 027       12/1990

* cited by examiner

*Primary Examiner*—Robert Dawson
*Assistant Examiner*—Jeffrey B. Robertson
(74) *Attorney, Agent, or Firm*—Michael P. Dilworth

(57) ABSTRACT

Shear stable aqueous emulsion of amino modified siloxanes may be made by the addition of a mono acid to the emulsion. These compositions may include acids such as (a) hydroxy carboxylic acids; (b) amino dicarboxylic acids; (c) amic acids; (d) monoesters of dicarboxylic acids; (e) monoesters of di-inorganic acids; and (f) diesters of tri-inorganic acids.

14 Claims, No Drawings

200
SHEAR STABLE AMINOSILICONE EMULSIONS

FIELD OF THE INVENTION

The present invention relates to a shear stable aqueous emulsion of a polysiloxane containing at least one amino group per molecule and a mono acid. The present invention also relates to an aqueous emulsion which when applied to fibrous substrate imparts softness to the substrate.

BACKGROUND OF THE INVENTION

Many aqueous emulsions containing organomodified polysiloxanes are used in the textile and paper industry to impart softness to the substrates. The polysiloxane emulsions usually are applied to textiles and papers using a padder, a kiss roller or a spraying nozzle, thus the polysiloxane emulsions are subjected to a certain extent of shear depending on the application method. Since the polysiloxane emulsions are heterogeneous mixtures containing small droplets of polysiloxane oils in water, coalescence of oil droplets to cream or surface oil occurs when the shear condition is severe enough. This not only causes problems in the manufacturing process, it also may result in deposit of the polysiloxane oils on textiles and papers and increase rejects. Therefore, a shear stable polysiloxane emulsion is very important in the application of polysiloxane emulsions.

The use of certain acids, e.g., citric acid, in the preparation of aminosilicone emulsions is known, but only to modify the pH of the emulsion, not to impart any stability to it. See e.g., U.S. Pat. No. 4,601,902 to Fridd et al. Acids also have been used to neutralize catalysts in emulsion polymerization systems containing aminosiloxanes, but the aminosiloxane herein are cross-linkable, reactive species, and the the neutralization is of the catalyst, not the siloxane or the emulsion. See, e.g., U.S. Pat. No. 4,894,412 to Okada et al. The selection of the particular acid is important in that certain acids will not provide benefits for shearing properties of the emulsion.

SUMMARY OF THE INVENTION

The present invention provides a method for the preparation of a shear stable aqueous emulsion comprising a polysiloxane containing at least one amino group per molecule ("amino polysiloxane"), and a mono acid. The aqueous emulsion, when applied to a fibrous substrate, imparts softness to the substrate. Preferred acids used herein, include, but are not limited to (a) hydroxy carboxylic acids; (b) amino dicarboxylic acids; (c) amic acids; (d) monoesters of dicarboxylic acids; (e) monoesters of di-inorganic acids; and (f) diesters of tri-inorganic acids.

DETAILED DESCRIPTION OF THE INVENTION

Aminopolysiloxane

The aminopolysiloxane has at least one amino or substituted amino group linked to a siloxy unit through an organic bridge that is bonded to the silicon atom of the siloxy unit by a carbon-to-silicon bond. The aminopolysiloxanes may be linear, branched or cyclic. They may have a viscosity ranging from about 1 to 20,000 centipoises measured at 25° C., preferably, about 10 to 10,000 at 25° C. The aminopolysiloxanes preferably have an amine content ranging from about, 0.05% to 3%, by weight, preferably from about 0.1% to 2% by weight as measured as $NH_2$. The aminopolysiloxanes may contain other functionalities, e.g., polyether. The aminopolysiloxane may be linear or branched or even by alternating linkages of aminoalkyl functionality and siloxane functionality; however, they should not contain reactive silanol (i.e., Si-OH) which would cause the aminopolysiloxane to crosslink in the emulsion. The preferred aminopolysiloxane is a linear structure illustrated by Formula $MD_aD^*_bM$ wherein D is $O_{1/2}Si(CH_3)_2O_{1/2}$; $D^*$ is $O_{1/2}Si(CH_3)QO_{1/2}$; and M is $O_{1/2}SiQ_j(CH_3)_{3-j}$, a ranges in value from about 0 to 1,000, and most preferably a ranges in value from about 0 to 500; j=0 or 1; and b ranges in value from about 0 to 100, preferably b ranges in value from about 1 to 50, most preferably b ranges in value from about 1 to 20, b+j>0 and a/(b+j) is 0.5 to 5.

Q is a polyether, polyhydric, amine, epoxy, alkyl of $C_2$–$C_{18}$, or alkanol, but at least one Q is an amine containing group Z. The group Z is of the formula $BN[B_1O(C_dH_{2d}O)_eR]_{2-z}V_z$, where each d is 2 to 4, preferably 2 to 3, each e is 0 to 15, preferably 0 to 8, z=0 to 2, preferably 2, each V is a univalent group, $B_1$ is an alkylene divalent bridging group on which there may be hydroxyl substituents, and B is a divalent bridging group.

V groups preferably are alkyl (which may be branched, linear or cyclic) of less than 8 carbons, which may or may not contain hydroxyl functionalities. Another preferred V is an alkyl amine functionality, the nitrogen of which may be further substituted (e.g., with an alkyl) or be further alkoxylated. Exemplary V are ethyl, ethanol, propanol, methyl, and ethyl amine.

B groups may be of the formula $B_1(O)_y(C_dH_{2d}O)_jB_1$ wherein $B_1$ and d are as above, j=0 to 6, preferably 0 to 2, and y=0 or 1. Preferably $B_1$ has 2 to 6 carbon atoms. B may also be a hydroxyl-substituted acyclic alkylene group of two to eight carbon atoms and is illustrated by 2-hydroxypropylene, i.e., —$CH_2CH(OH)CH_2$—, or B is a hydroxyl-substituted cyclic alkylene group having no more than eight carbon atoms, e.g., 2-hydroxycyclohexylene,

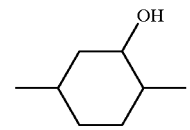

of which the cyclic groups having three to six carbon atoms are preferred

When Q or B is a mixture of oxyalkylenes, it may be blocked or random. One skilled in the art will understand the advantages in the position of the oxyethylene relative to the oxypropylene, when the alkyleneoxide group is blocked.

Also contemplated herein are quaternary versions of Z, but said quaternary compounds are not preferred for use in the present invention.

Preferred Z structures are wherein R is hydrogen or methyl, $B_1$ is a divalent organic group of 2 to 4 carbons, B is a divalent organic group of 2 to 4 carbons, in which at least one carbon radical contains a hydroxyl group, and V is 2-hydroxyethyl, 2-hydroxypropyl, 3-hydroxypropyl, propyl, ethyl or methyl. Exemplary amine groups for Q are:

—$C_3H_6NH_2$
—$C_3H_6N(C_2H_5)_2$
—$CH_2CH_2C(CH_3)_2NH_2$
—$C_3H_6N(CH_2CH_2OH)_2$
—$C_3H_6N(CH_3)CH_2CH_2NH_2$
—$C_3H_6NHCH_2CH_2NH_2$
—$C_3H_6OCH_2CH(OH)CH_2NH_2$
—$C_3H_6$—$N(CH_2CH_2OH)(CH_2CH_2NH_2)$
—$C_3H_6OCH_2CH(OH)CH_2NHCH_2CH_2NH_2$

Those functionalities with free hydroxyls may be further alkoxylated with ethylene oxide and propylene oxide.

Aminopolysiloxanes employed in the present invention are commercially available from Witco Corporation.; Alternatively, aminopolysiloxanes used in the present invention can be prepared by the procedures disclosed in U.S. Pat. Nos. 3,033,815; 3,146,250, 3,355,454 and 4,247,592.

Mono Acid

Mono acids which are soluble or dispersible in water and thus, compatible with the aqueous emulsion containing the aminopolysiloxane can be employed in the present invention. In its broadest aspect, the mono acid of the present invention is selected from the group consisting of (i) inorganic mono acids; (ii) organic (i.e., carboxylic) mono acids and (iii) mixtures thereof. The acids need to be proton donors to the amine (pKa<6) and therefore the inorganic acid must be a Bronstead acid and the organic acid a carboxylic acid. Illustrative inorganic mono acids include hydrochloric acid, perchloric acid and nitric acid.

Mono inorganic acids which are preferred are those which are monoesters of a di-inorganic acid, e.g., $HSO_4R$ wherein R is an alkyl, alkaryl or aryl, or diesters of tri-inorganic acids, e.g., $HPO_4R_2$. It is noted that the salts of such acids do not function well as compared to the esters.

The organic mono acids contain one equivalence of a carboxylic acid, i.e., of the structure $R^5C(=O)OH$, wherein $R^5$ is hydrogen or a neutral monovalent hydrocarbon and includes alkyl such as methyl, ethyl, propyl, butyl and the like; aryl such as phenyl and tolyl; aralkyl such as benzyl; and groups wherein one or more hydrogen atoms of the above mentioned groups are substituted with hydroxy, or halogen. Illustrative organic mono acids include formic acid, and acetic acid.

$R^5$ could include other acid groups (i.e., carboxyls), but in such a case the cumulative to effect of the substitutions on $R^5$ should not result in any additional acid or base (i.e., for every carboxyl there must be an amine or the carboxyl must be substituted to form an ester or amide). For example, classes of preferred organic acids are hydroxy carboxylic acids, monoesters of dicarboxylic acids, amic acids (monoamides of dicarboxylic acids) and amino dicarboxylic acids. Specific amino dicarboxylic acids are α-aminoadipic acid, aspartic acid, and glutamic acid. Specific hydroxy carboxylic acids are glycolic acid, lactic acid, β-hydroxybutyric acid, and hydroxybenzoic acid. Specific monoesters of dicarboxylic acids are monomethyl succinate, monoethyl succinate and monoethyl malonic acid. Specific examples of amic acids are N-methyl succiniamic acid and maliamic acid.

Optional Additives

Some optional additives in the emulsion are amino/epoxy/siloxy terpolymers, polyether modified polysiloxanes, solvents (alcohol, mineral oil, silicone oil, or glycol ethers (e.g., butyl cellusolve)), epoxy/polyether/siloxy terpolymers, preservatives, fillers, colorants, biocides, biostats, silicone antifoams, perftime, viscosity modifier; waxes (parafins or polyethylene), emoliants, binders (latex), self-dispersing hydrophilic softening agents and freeze thaw additives (e.g., glycols).

Emulsion Preparation

The preparation of a shear stable emulsion is accomplished by the addition of the mono acid, preferably an aqueous solution of the water soluble mono acid, to an aqueous emulsion of the aminopolysiloxane with mixing or blending. The mixing or blending need not be under high shear or elevated temperature, but may be simple mixing.

The preparations of the emulsion of the aminopolysiloxane are known in the art. A preferred way to do this is by adding the aminosiloxane slowly under high shear to a water/surfactant mixture until a fine grease is formed. Water should be added then to invert the emulsion to form an oil in water emulsion. Lastly, the acid should be added.

Typical emulsifiers which can be used in the preparation of the aminopolysiloxane emulsion include nonionic, amphoteric (including zwitterionic), cationic and anionic surfactants. Examples of nonionic surfactants include polyoxyethylene alkyl ether, polyoxyethylene alkylphenol ether, polyoxyethylene alkyl ester, polyoxyethylene sorbitan alkyl ester, polyalkylene glycol, and polyalkylerie glycol modified polysiloxanes. Examples of cationic surfactants include quaternary ammonium salts such as alkyltrimethylammonium hydroxide, dialkyldimethylammonium hydroxide, and trialkyl hydroxyethylammonium methosulfate. Examples of amphoteric surfactants are betaine derivatives, imidazolines, N-alkyl iminodiesters, cocoamine oxide, and dicarboxylic carboxy glycinate. Examples of anionic surfactants include sulfate and sulfonate salts such as sodium alkylsulfate, alkanolammonium alkylsulfate, sodium alkylarylsulfonate and alkanolammonium alkylarylsulfonate. Specific examples are SPAN (ICI), TWEEN (ICI), WITCONOL (Witco), REWOTERIC (Witco) and tridecyl alcohol ethoxylates. The surfactants should be present at 5–40% by weight based on the amount of amino polysiloxane, preferably 10 to 20 weight percent.

The emulsion may be buffered with salts of the acid to be used to ensure the maintenance of the pH of the emulsion within 4.5 to 9.5, preferably 6.5 to 8.5. Suitable buffers include sodium acetate, sodium propionate, sodium glycolate, and sodium glutamate.

The amount of the aminopolysiloxane in the total final emulsion ranges from 0.1 to 75 parts by weight based on 100 parts of the total emulsion, and preferably 1 to 40 parts by weight based on 100 parts of the total emulsion. At least about 0.01% to about 1.5% amine content based on the total weight of the total emulsion should be present. Preferably, the amine content ranges from about 0.05% to 1%, and most preferably it ranges from about 0.05% to 0.5%.

The amount of the mono acid depends on the amine content of the total emulsion. The amount of the mono acid ranges from about 0.05 equivalents to about 1.5 equivalents for every equivalent amount of amine in the total emulsion. Preferably, the amount of the mono acid ranges from 0.1 to 1 equivalent for every equivalent amount of amine in the total emulsion. Most preferably, there should be a molar equivalency of acid functionality to amino functionality.

Emulsion Application to Textiles and Papers

The present invention results in shear stable aminopolysiloxane aqueous emulsions, i.e., emulsion which do not show any surface oil or creaming or after the shear stability. The particle size in the emulsion should be less than 1.0 μm, preferably less than 0.5 μm. The emulsion may be translucent or opaque.

The shear stable emulsion composition can be diluted with water to a desired solids level and applied Onto fibrous substrates (which can be woven or non-woven) such as textiles and papers. Suitable application methods include printing, spraying, dipping or kiss roll application. The composition may be applied as a concentrate, but it will be more common to prepare the emulsion at a higher solids content to reduce shipping and/or handling costs and then dilute the formulation with water just prior to use. After the substrate is dried either at room temperature or by heat, it additionally can be optionally cured to crosslink at a temperature less than the melting or decomposition temperature of the substrate. Heating can be done by.any suitable method, but preferably is done by passing the substrate through a hot air oven. The resulting treated substrate thus has properties such as softness and compression resistance.

The fibrous: substrate which can be treated with the emulsion of the present invention is exemplified by natural fibers such as cotton, flax, silk, cellulose and wool; synthetic fibers such as polyester, polyamide, polyacrylonitrile, polyethylene, polypropylene and polyurethane; and inorganic fibers such as glass fiber and carbon fiber. Blends of any of the foregoing are also potential substrates.

These emulsions also may be use in personal care (e.g., hair care, and skin care products), car polishes, leather protectants, and shine and gloss protectants. Preferably, the emulsion is applied onto tissue, paper towels, wipes, etc. Methods for such applications are disclosed in U.S. Pat. No. 5,573,637 to Ampulski; U.S. Pat. No. 5,389,204 to Ampulski; U.S. Pat. No. 5,246,546 to Ampulski; U.S. Pat. No. 5,215,626 to Ampulski; and U.S. Pat. No. 5,529,665 to Kaun, which are incorporated herein by reference.

The following examples are set forth to illustrative purposes only and not to be construed as unduly limiting of the present invention. All parts and percentages are by weight unless otherwise specified.

EXPERIMENTS

Description of Test Methods

Test Method for Shear Stability

The following method is used to determine the shear stability of an aminopolysiloxane emulsion. A shear stable aminopolysiloxane emulsion does not show any surface oil or creaming on or after the shear stability. A 400 g sample of an aminopolysiloxane emulsion is placed in a plastic container with a 7.5 inch (~19 cm) inner diameter. The container then is placed under a Lightnin mixer mounted with a 6 inch (~15 cm) diameter Cowles blade. The sample is sheared with the Cowles blade at 2,000 rpm for 1 hour. The sheared emulsion is examined for surface oil and creaming.

Creaming is a process of emulsion droplets floating upwards to form a concentrated emulsion (cream), quite distinct from the underlying dilute emulsion. Surface oil is when the emulsion droplets coalesce to form oil which then floats to the surface of the emulsion.

Example 1

Emulsion I was prepared by blending 50 parts of an aminopolysiloxane of 40,000 molecular weight which contains 0.25% by weight amine, 40.7 parts of water and 9.3 parts of a blend of polyethyleneoxide alkyl ethers having an HLB of 12–13.

To 60 parts of Emulsion I, 0.5 part of a 10% aqueous HCl solution, 1 part of a 10% aqueous NaCl solution and 38.5 parts of water were added. The resulting emulsion was milky white and stable at room temperature. No creaming or surface oil was detected in the sheared emulsion. The sheared emulsion maintained one phase and stable at room temperature.

Comparative Example A

To 60 parts of Emulsion I, 40 parts of water were added. The resulting emulsion was milky white and stable at room temperature. After shearing, the emulsion broke down to three phases: (1) surface oil which amounts to approximately 10% of the total material, (2) cream phase which amounts to about 10% of the total material, and (3) emulsion phase which amounts to about 80% of the total material.

Comparative Example B

To 60 parts of Emulsion I, 0.7 part of a 10% aqueous sulfuric acid solution, 1 part of a 10% aqueous sodium sulfate solution and 38.3 parts of water were added. The resulting emulsion was milky. white and stable at room temperature. After the shear test, the emulsion broke down to three phases: (1) some surface oil floating on top of the cream phase, (2) cream phase which amounts to about 50% of the total material, and (3) emulsion phase which amounts to about 50% of the total material.

Example 2

To 60 parts of Emulsion I, 2.3 parts of a 10% aqueous glycolic acid solution, 0.4 parts of a 10% aqueous sodium hydroxide solution and 37.3 parts of water were added. The resulting emulsion was translucent and stable at room temperature. After shearing, no creaming or surface oil was detected. The emulsion maintained its homogeneous translucent appearance and was stable at room temperature.

Comparative Example C

To 60 parts of Emulsion I, 2.4 parts of a 10% aqueous succinic acid solution, 0.5 parts of a 10% aqueous sodium hydroxide solution and 37.1 parts of water were added. The resulting emulsion was milky white and stable at room temperature. After the shear test, the emulsion broke down to three phases: (1) some surface oil floating on top of the cream phase, (2) cream phase which amounts to about 40% of the total material, and (3) emulsion phase which amounts to about 60% of the total material.

Example 3

To 60 parts of Emulsion I, 1.5 parts of a 10% aqueous acetic acid solution, 1 part of a 10% aqueous sodium acetate solution and 37.5 parts of water were added. The resulting emulsion was translucent and stable at room temperature. After shearing no creaming or surface oil was detected. The emulsion had a homogeneous translucent appearance and was stable at room temperature.

Example 4

To 60 parts of Emulsion I, 3 parts of a 10% aqueous acetic acid solution, 1 part of a 10% aqueous sodium acetate solution and 36 parts of water were added. The resulting emulsion was milky white and stable at room temperature. After shearing no creaming or surface oil was detected. The emulsion maintained its homogeneous appearance and was stable at room temperature.

Example 5

To 60 parts of Emulsion I, 26.8 parts of a 0.75% aqueous solution of L-glutamic acid, 1 part of a 10% aqueous sodium glutamate solution and 12.2 parts of water were added. The resulting emulsion was milky white and stable at room temperature. After shearing no creaming or surface oil was detected. The emulsion maintained one phase and stable at room temperature.

Example 6

To 60 parts of Emulsion I, 28.6 parts of a 1% aqueous hydroxybenzoic acid solution, 1 part of a 10% aqueous sodium hydroxide and 11.1 parts of water were added. The resulting emulsion was milky white and stable at room temperature. After shearing no creaming or surface oil was detected in the sheared emulsion. The emulsion maintained one phase and stable at room temperature.

Example 7

To 60 parts of Emulsion I, 1.5 parts of a 10% aqueous acetic acid solution, 1 part of a 10% aqueous sodium acetate solution, 1 part of a 12,500 molecular weight polyoxyalkylene polysiloxane copolymer which is 88% by weight polyether, and 36.5 parts of water were added. The resulting emulsion was translucent and stable at room temperature. After shearing no creaming or surface oil was detected. The emulsion maintained its homogeneous translucent appearance and stable at room temperature.

We claim:

1. A composition comprising:
   a. water;
   b. an amino polysiloxane; and
   c. a mono acid selected from the group consisting of: amic acids; monoesters of di-inorganic acids and diesters of tri-inorganic acids.

2. A composition according to claim 1 additionally comprising an emulsifier.

3. A composition according to claim 1 wherein the acid is an amic acid.

4. A composition according to claim 1 wherein the acid is a monoester of a di-inorganic acid.

5. A composition according to claim 1 wherein the acid is a diester of a tri-inorganic acid.

6. A composition comprising:
   a. water;
   b. an amino polysiloxane having a polyether functionality; and
   c. a mono acid selected from the group consisting of: hydroxy carboxylic acids, monoesters of dicarboxylic acids, amic acids; monoesters of di-inorganic acids; diesters of tri-inorganic acids and amino dicarboxylic acids.

7. A composition comprising:
   a. water;
   b. an amino polysiloxane; and
   c. a hydroxy carboxylic acid selected from the group consisting of β-hydroxybutyric acid and hydrobenzoic acid.

8. The composition of claim 7 further comprising an emulsifier.

9. A composition according to any of claims 1, 6, or 7 wherein the siloxane has a viscosity of from about 1 to 20,000 centipoises measured at 25° C., an amine content ranging from about 0.01% to 3% and has no silanol groups.

10. A composition according to claim 9 wherein the siloxane is

wherein

D is $O_{1/2}Si(CH_3)_2O_{1/2}$;

D* is $O_{1/2}Si(CH_3)QO_{1/2}$;

M is $O_{1/2}SiQ_j(CH_3)_{3-j}$;

a ranges in value from about 0 to 1,000;

j=0 or 1;

b ranges in value from about 0 to 100;

b+j>0;

a/(b+j) is 0.5 to 5;

Q is a functional group comprising a polyether, polyhydric, amine, epoxy, alkyl of $C_2$–$C_{18}$, or alkanol group, provided that at least one Q comprises an amine group.

11. A composition as in claim 10 wherein the Q group comprising an amine group has the formula:

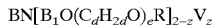

where each d is 2 to 4, each e is 0 to 15, z=0 to 2,

R is H or methyl, each V is a univalent group, $B_1$ is an alkylene divalent bridging group on which there may be hydroxyl substituents, and B is a divalent bridging group.

12. A composition as in claim 11 wherein d is 2 to 3, e is 0 to 8 and z is 2.

13. A process comprising applying a composition as in any of claims 1, 6 or 7 to a cellulosic fabric.

14. The composition of claim 8 wherein said emulsifier is composed only of a non-ionic surfactant.

* * * * *